US011514576B2

(12) United States Patent
Shameli et al.

(10) Patent No.: US 11,514,576 B2
(45) Date of Patent: Nov. 29, 2022

(54) SURGICAL SYSTEM WITH COMBINATION OF SENSOR-BASED NAVIGATION AND ENDOSCOPY

(71) Applicants: Acclarent, Inc., Irvine, CA (US); Biosense Webster (Israel) Ltd., Yokneam (IL)

(72) Inventors: Ehsan Shameli, Irvine, CA (US); Jetmir Palushi, Irvine, CA (US); Fatemeh Akbarian, Rancho Palos Verdes, CA (US); Yehuda Algawi, Binyamina (IL); Assaf Govari, Haifa (IL); Babak Ebrahimi, Irvine, CA (US)

(73) Assignees: Acclarent, Inc., Irvine, CA (US); Biosense Webster (Israel) Ltd., Yokneam (IL)

( * ) Notice: Subject to any disclaimer, the term of this patent is extended or adjusted under 35 U.S.C. 154(b) by 403 days.

(21) Appl. No.: 16/665,133

(22) Filed: Oct. 28, 2019

(65) Prior Publication Data
US 2020/0193600 A1    Jun. 18, 2020

Related U.S. Application Data

(60) Provisional application No. 62/779,614, filed on Dec. 14, 2018.

(51) Int. Cl.
*G06T 7/00* (2017.01)
*A61B 1/00* (2006.01)
(Continued)

(52) U.S. Cl.
CPC ........ *G06T 7/0016* (2013.01); *A61B 1/00009* (2013.01); *A61B 1/05* (2013.01);
(Continued)

(58) Field of Classification Search
CPC ................... G06T 7/0016; G06T 7/80; G06T 2207/10068; G06T 2207/30004;
(Continued)

(56) References Cited

U.S. PATENT DOCUMENTS 7,720,521 B2    5/2010 Chang et al.
10,561,370 B2   2/2020 Salazar et al.
(Continued)

FOREIGN PATENT DOCUMENTS

WO    WO 2014/140813 A1    9/2014

OTHER PUBLICATIONS

International Search Report and Written Opinion dated May 19, 2020 for International Application No. PCT/IB2019/060537, 12 pages.

*Primary Examiner* — Emily C Terrell
*Assistant Examiner* — Molly Wilburn
(74) *Attorney, Agent, or Firm* — Frost Brown Todd LLC

(57) ABSTRACT

A set of pre-operative images may be captured of an anatomical structure using an endoscopic camera. Each captured image is associated with a position and orientation of the camera at the moment of capture using image guided surgery (IGS) techniques. This image data and position data may be used to create a navigation map of captured images. During a surgical procedure on the anatomical structure, a real-time endoscopic view may be captured and displayed to a surgeon. The IGS navigation system may determine the position and orientation of the real-time image; and select an appropriate pre-operative image from the navigation map to display to the surgeon in addition to the real-time image.

20 Claims, 7 Drawing Sheets

(51) Int. Cl.
*G06T 7/80* (2017.01)
*A61B 34/00* (2016.01)
*A61B 1/05* (2006.01)
*A61B 5/06* (2006.01)
*A61B 1/233* (2006.01)
*H04N 5/225* (2006.01)
*A61B 17/24* (2006.01)

(52) U.S. Cl.
CPC .............. *A61B 1/233* (2013.01); *A61B 5/062* (2013.01); *A61B 17/24* (2013.01); *A61B 34/25* (2016.02); *G06T 7/80* (2017.01); *H04N 5/2253* (2013.01); *A61B 2034/254* (2016.02); *G06T 2207/10068* (2013.01); *G06T 2207/30004* (2013.01)

(58) Field of Classification Search
CPC . G06T 2207/30028; G06T 2207/30092; G06T 7/248; G06T 2207/30244; A61B 1/00009; A61B 1/05; A61B 1/233; A61B 5/062; A61B 17/24; A61B 34/25; A61B 2034/254; A61B 1/000094; A61B 90/361; A61B 2034/105; A61B 2034/2048; A61B 2034/2051; A61B 2034/2072; A61B 2090/364; A61B 2090/365; A61B 34/20; A61B 1/0005; A61B 1/00193; A61B 1/00194; H04N 5/2253; H04N 5/265; H04N 2005/2255

See application file for complete search history.

(56) References Cited

U.S. PATENT DOCUMENTS

| | | |
|---|---|---|
| 2005/0272971 A1 | 12/2005 | Ohnishi et al. |
| 2006/0184016 A1* | 8/2006 | Glossop ............... A61B 1/2676 600/434 |
| 2006/0241405 A1 | 10/2006 | Leitner et al. |
| 2007/0078334 A1* | 4/2007 | Scully ..................... A61B 5/06 600/424 |
| 2011/0270084 A1 | 11/2011 | Choi et al. |
| 2013/0296682 A1 | 11/2013 | Clavin et al. |
| 2014/0128727 A1* | 5/2014 | Daon ..................... A61C 1/082 600/424 |
| 2014/0160264 A1* | 6/2014 | Taylor ..................... A61F 9/008 348/79 |
| 2014/0364725 A1 | 12/2014 | Makower |
| 2015/0182106 A1 | 7/2015 | King |
| 2016/0000517 A1* | 1/2016 | Kehat .................... A61B 34/25 600/103 |
| 2016/0008083 A1 | 1/2016 | Kesten et al. |
| 2016/0022125 A1* | 1/2016 | Nicolau ................. A61B 34/20 600/109 |
| 2017/0265943 A1* | 9/2017 | Sela ....................... A61B 34/10 |
| 2017/0265947 A1* | 9/2017 | Dyer ...................... A61B 6/501 |
| 2017/0372640 A1* | 12/2017 | Lampotang .......... G09B 23/285 |
| 2020/0297430 A1* | 9/2020 | Cameron ................ A61B 6/12 |

* cited by examiner

SURGICAL SYSTEM WITH COMBINATION OF SENSOR-BASED NAVIGATION AND ENDOSCOPY

PRIORITY

This application claims priority to U.S. Provisional Pat. App. No. 62/779,614, entitled "Surgical System with Combination of Sensor-Based Navigation and Endoscopy," filed Dec. 14, 2018, the disclosure of which is incorporated by reference herein in its entirety.

BACKGROUND

Image-guided surgery (IGS) is a technique where a computer is used to obtain a real-time correlation of the location of an instrument that has been inserted into a patient's body to a set of preoperatively obtained images (e.g., a CT or MRI scan, 3-D map, etc.), such that the computer system may superimpose the current location of the instrument on the preoperatively obtained images. An example of an electromagnetic IGS navigation systems that may be used in IGS procedures is the CARTO® 3 System by Biosense-Webster, Inc., of Irvine, Calif. In some IGS procedures, a digital tomographic scan (e.g., CT or MRI, 3-D map, etc.) of the operative field is obtained prior to surgery. A specially programmed computer is then used to convert the digital tomographic scan data into a digital map. During surgery, special instruments having sensors (e.g., electromagnetic coils that emit electromagnetic fields and/or are responsive to externally generated electromagnetic fields) are used to perform the procedure while the sensors send data to the computer indicating the current position of each surgical instrument. The computer correlates the data it receives from the sensors with the digital map that was created from the preoperative tomographic scan. The tomographic scan images are displayed on a video monitor along with an indicator (e.g., crosshairs or an illuminated dot, etc.) showing the real-time position of each surgical instrument relative to the anatomical structures shown in the scan images. The surgeon is thus able to know the precise position of each sensor-equipped instrument by viewing the video monitor even if the surgeon is unable to directly visualize the instrument itself at its current location within the body.

The use of IGS navigation may significantly increase the safety and success of surgical procedures. As one example, a surgeon may be able to more precisely position instruments at an anatomical structure. The virtual view provided by an IGS navigation system may also be displayed along with actual video and images captured by an endoscope (e.g., a standalone endoscope or an endoscope integrated with another surgical instrument in use at the surgical site). With pre-operatively obtained topographical images used to simulate the virtual view and instrument positions, and real-time images of surgical site during a procedure, a surgeon has a wide range of inputs that may be considered during a procedure in order to guide their actions and determine when the procedure is complete. Even so, the pre-operative images are limited in some ways, since they are typically produced using indirect imaging techniques. As an example, rather than capturing reflected light directly from an object as a camera does and producing a full color photorealistic image of the object, IGS navigation pre-operative images are produced by interpreting various non-visual factors such as magnetism, radio waves, x-rays, or ionizing radiation.

While the resulting image sets are useful in many applications, they may not capture some aspects of an anatomical structure (e.g., color, texture, and other surface characteristics), and may have reduced resolution and clarity as compared to direct image capture. While endoscope images may provide such additional details and clarity, the endoscopic view is limited to real-time images of the anatomical structure in its current state. Any such limitation on the information available to a surgeon during a procedure may contribute to a negative outcome, which may require follow-up and corrective procedures.

While several systems and methods have been made and used in surgical procedures, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

Figure 1:
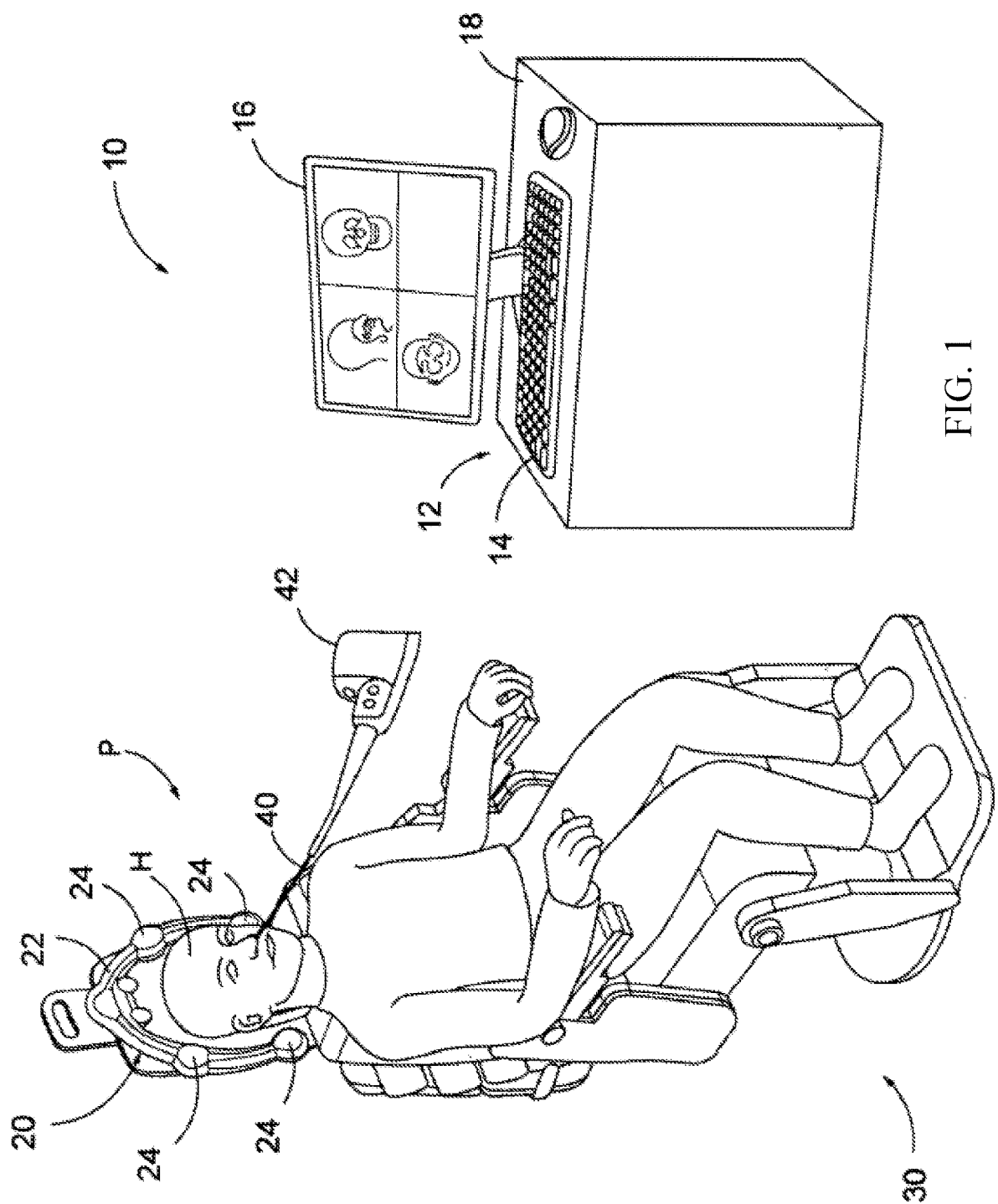
FIG. 1 depicts a schematic view of an exemplary surgery navigation system being used on a patient seated in an exemplary medical procedure chair.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

I. EXEMPLARY IMAGE GUIDED SURGERY NAVIGATION SYSTEM

When performing a medical procedure within a head (H) of a patient (P), it may be desirable to have information regarding the position of an instrument within the head (H) of the patient (P), particularly when the instrument is in a location where it is difficult or impossible to obtain an endoscopic view of a working element of the instrument within the head (H) of the patient (P). FIG. 1 shows an exemplary IGS navigation system (10) enabling an ENT procedure to be performed using image guidance. In addition to or in lieu of having the components and operability described herein IGS navigation system (10) may be constructed and operable in accordance with at least some of the teachings of U.S. Pat. No. 7,720,521, entitled "Methods and Devices for Performing Procedures within the Ear, Nose, Throat and Paranasal Sinuses," issued May 18, 2010, the disclosure of which is incorporated by reference herein; and U.S. Pat. Pub. No. 2014/0364725, entitled "Systems and Methods for Performing Image Guided Procedures within the Ear, Nose, Throat and Paranasal Sinuses," published Dec. 11, 2014, now abandoned, the disclosure of which is incorporated by reference herein.

IGS navigation system (10) of the present example comprises a field generator assembly (20), which comprises set of magnetic field generators (24) that are integrated into a horseshoe-shaped frame (22). Field generators (24) are operable to generate alternating magnetic fields of different frequencies around the head (H) of the patient (P). A navigation guidewire (40) is inserted into the head (H) of the patient (P) in this example. Navigation guidewire (40) may be a standalone device or may be positioned on an end effector or other location of a medical instrument such as a surgical cutting instrument or dilation instrument. In the present example, frame (22) is mounted to a chair (30), with the patient (P) being seated in the chair (30) such that frame (22) is located adjacent to the head (H) of the patient (P). By way of example only, chair (30) and/or field generator assembly (20) may be configured and operable in accordance with at least some of the teachings of U.S. patent application Ser. No. 15/933,737, entitled "Apparatus to Secure Field Generating Device to Chair," filed Mar. 23, 2018, issued as U.S. Pat. No. 10,561,370 on Feb. 18, 2020, the disclosure of which is incorporated by reference herein.

IGS navigation system (10) of the present example further comprises a processor (12), which controls field generators (24) and other elements of IGS navigation system (10). For instance, processor (12) is operable to drive field generators (24) to generate alternating electromagnetic fields; and process signals from navigation guidewire (40) to determine the location of a sensor in navigation guidewire (40) within the head (H) of the patient (P). Processor (12) comprises a processing unit communicating with one or more memories. Processor (12) of the present example is mounted in a console (18), which comprises operating controls (14) that include a keypad and/or a pointing device such as a mouse or trackball. A physician uses operating controls (14) to interact with processor (12) while performing the surgical procedure. In some implementations, processor (12) may include one or more memories and processing units, which may be distributed across one or more separate computing devices positioned proximately to the IGS navigation system (10) (e.g., one or more computers within the surgical suite), located remotely from the IGs navigation system (10) (e.g., one or more remote servers, virtual servers, or cloud servers in communication with the IGS navigation system (10) across a network), or combinations thereof. In such implementations, different tasks may be handled by different sub-components or sub-processors of the processor (12), for example, a computer, processor, and memory within the surgical suite may process and provide instrument tracking features, while a remotely located server may receive endoscopic images, topographic images, and other images and apply image processing, storage, encryption, or other tasks to received images.

Navigation guidewire (40) includes a sensor (not shown) that is responsive to positioning within the alternating magnetic fields generated by field generators (24). A coupling unit (42) is secured to the proximal end of navigation guidewire (40) and is configured to provide communication of data and other signals between console (18) and navigation guidewire (40). Coupling unit (42) may provide wired or wireless communication of data and other signals.

In the present example, the sensor of navigation guidewire (40) comprises at least one coil at the distal end of navigation guidewire (40). When such a coil is positioned within an alternating electromagnetic field generated by field generators (24), the alternating magnetic field may generate electrical current in the coil, and this electrical current may be communicated along the electrical conduit(s) in navigation guidewire (40) and further to processor (12) via coupling unit (42). This phenomenon may enable IGS navigation system (10) to determine the location of the distal end of navigation guidewire (40) or other medical instrument (e.g., dilation instrument, surgical cutting instrument, etc.) within a three-dimensional space (i.e., within the head (H) of the patient (P), etc.). To accomplish this, processor (12) executes an algorithm to calculate location coordinates of the distal end of navigation guidewire (40) from the position related signals of the coil(s) in navigation guidewire (40). While the position sensor is located in guidewire (40) in this example, such a position sensor may be integrated into various other kinds of instruments, including those described in greater detail below.

Processor (12) uses software stored in a memory of processor (12) to calibrate and operate IGS navigation system (10). Such operation includes driving field generators (24), processing data from navigation guidewire (40), processing data from operating controls (14), and driving display screen (16). In some implementations, operation may also include monitoring and enforcement of one or more safety features or functions of IGS navigation system (10). Processor (12) is further operable to provide video in real time via display screen (16), showing the position of the distal end of navigation guidewire (40) in relation to a video camera image of the patient's head (H), a CT scan image of the patient's head (H), and/or a computer generated three-dimensional model of the anatomy within and adjacent to the patient's nasal cavity. Display screen (16) may display such images simultaneously and/or superimposed on each other during the surgical procedure. Such displayed images may also include graphical representations of instruments that are inserted in the patient's head (H), such as navigation guidewire (40), such that the operator may view the virtual rendering of the instrument at its actual location in real time. By way of example only, display screen (16) may provide images in accordance with at least some of the teachings of U.S. Pub. No. 2016/0008083, entitled "Guidewire Navigation for Sinuplasty," published Jan. 14, 2016, issued as U.S. Pat. No. 10,463,242 on Nov. 5, 2019, the disclosure of which is incorporated by reference herein.

Figure 2:
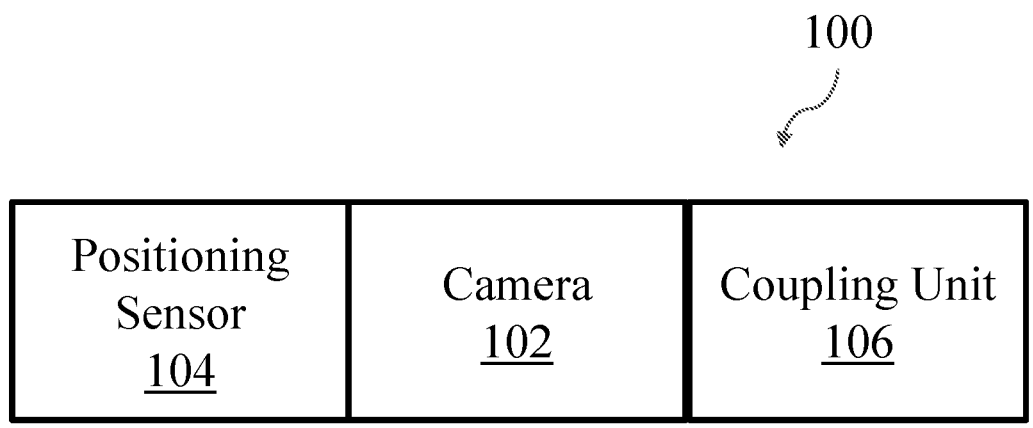
FIG. 2 depicts a schematic view of an exemplary endoscope usable with the surgery navigation system.

In the event that the operator is also using an endoscope, the endoscopic image may also be provided on display screen (16). For example, FIG. 2 shows a schematic view of an exemplary endoscope (100) usable with the IGS navigation system (10). The endoscope (100) includes a camera (102) operable to capture images and video, which may be positioned at the distal end of a rigid body or a flexible body (e.g., similar to the navigation guidewire (40)) that may be navigated into the nasal cavity to capture images at the surgical site. Also included is a position sensor (104) or tracking sensor proximate to the camera (102) and configured to be tracked by the IGS navigation system (10) (e.g., similar to the navigation guidewire (40)) in order to determine the position, orientation, or both of the camera (102). While instrument tracking techniques described above include the use of the field generator assembly (20) to produce a magnetic field that interacts with the position sensor in navigation guidewire (40) in order to enable position tracking, it should be understood that other types of position tracking exist and may be implemented with the technology disclosed herein. For example, in some cases a tracked area (e.g., such as the magnetic field) may instead be implemented using wireless beacon triangulation to communicate with and locate the position sensor (104) of endoscope (100) or other forms of wireless positioning and tracking capable of detection within a patient's body.

Power and information may be communicated via wires extending along the body of endoscope (100) to allow the operation of the camera (102), send or receive information to the position sensor (104), and receive images from the camera (102) as digital data (e.g., via a data connection) or optical data (e.g., via an optical fiber), for example. The endoscope (100) of the present example also includes a coupling unit (106) similar to the coupling unit (42), which may be configured to enable the use of the endoscope (100) with the IGS navigation system (10). This may include, for example, receiving signals from the position sensor (104) and communicating them to the processor (12) so that the location of the position sensor (104) may be determined, and receiving signals or data from the camera (102) and communicating them (e.g., in raw format as they are received, or after conversion, such as converting optical image data received via an optical fiber to digital image data prior to communication) to the processor (12) so that they may be displayed via the display screen (16).

While the position sensor (104) is described as being usable to determine position within three-dimensional space, it should be understood that some implementations of the position sensor (104) may also be usable to determine orientation within three-dimensional space (e.g., by use of a gyroscopic element, a combination of two or more independently tracked sensors such as orthogonal coils with a fixed relation to each other, or other similar means). Since the position sensor (104) may be usable to determine both position and orientation within the tracked area, it may at times also be referred to as a tracking sensor having one or both capabilities. In implementations where the position sensor (104) or another connected device or component is not capable of determining an orientation of the endoscope (100), the IGS navigation system (10) may determine the orientation automatically by assuming that the endoscope (100) is always oriented toward a particular anatomical target or other point within the surgical site.

The images provided through display screen (16) may help guide the operator in maneuvering and otherwise manipulating instruments within the patient's head (H) when such instruments incorporate a position sensor like position sensor (104). It should also be understood that other components of a surgical instrument and other kinds of surgical instruments, as described below, may incorporate a sensor like the sensor of navigation guidewire (40) or the sensor (104) of endoscope (100).

II. EXEMPLARY SYSTEM FOR COMPARATIVE NAVIGATION OF IMAGES

As has been described, an endoscope such as the endoscope (100) may be used with the IGS navigation system (10) in order to capture endoscopic images and video to be displayed on the display screen (16). Such endoscopic images may be displayed in isolation, in combination with other images (e.g., virtual endoscopic view, pre-operative CT image view, etc.), and with other information and interfaces as may be desired. One example of an interface that may be advantageously displayed via the display screen (16) may show a combination of pre-operative and either intra-operative or post-operative endoscopic images in order to show both the present appearance of a surgical site, as well as one or more past appearances of surgical site. In this manner, a surgeon may view the current appearance of the surgical site with additional context (e.g., one or more past appearance of the surgical site) that may be useful in determining whether presently performed operative steps have been successful or complete.

By way of example only, it may be desirable to compare pre-operative endoscopic images with intra-operative or post-operative endoscopic images of various anatomical structures within a nasal cavity after performing a medical procedure such as functional endoscopic sinus surgery (FESS), turbinate reduction, sinuplasty, or various other medical procedures as will be apparent to those skilled in the art in view of the teachings herein. Such visual comparisons may readily enable the operator to compare tissue structures before, during, and after the medical procedure, where the medical procedure resulted in remodeling or other modification of such tissue structures. By having endoscope position data directly incorporated into the pre-operative image data the most appropriate pre-operative images may be selected based on the real-time position of instrumentation during or after the medical procedure; or based on user selections made after the medical procedure.

Figure 3:
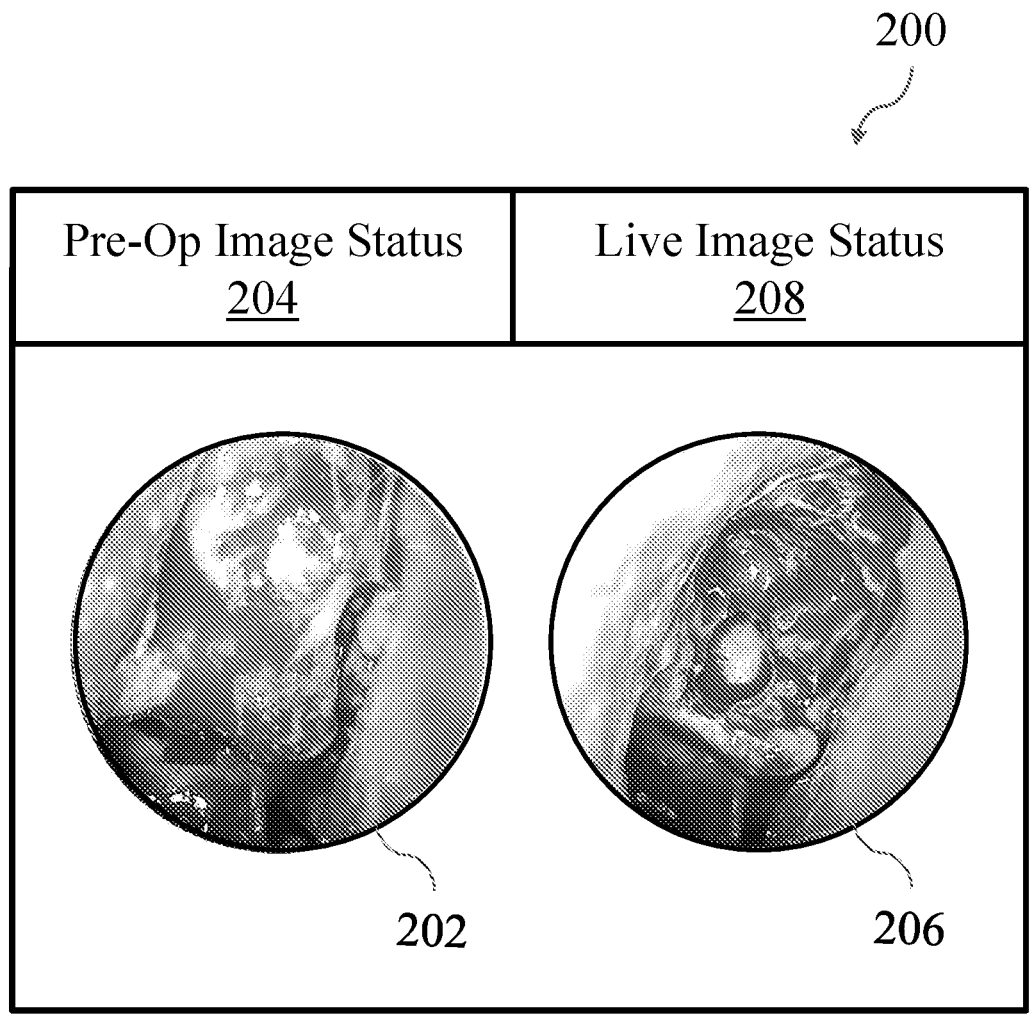
FIG. 3 depicts a simulated screenshot of an exemplary comparative interface.
Figure 4:
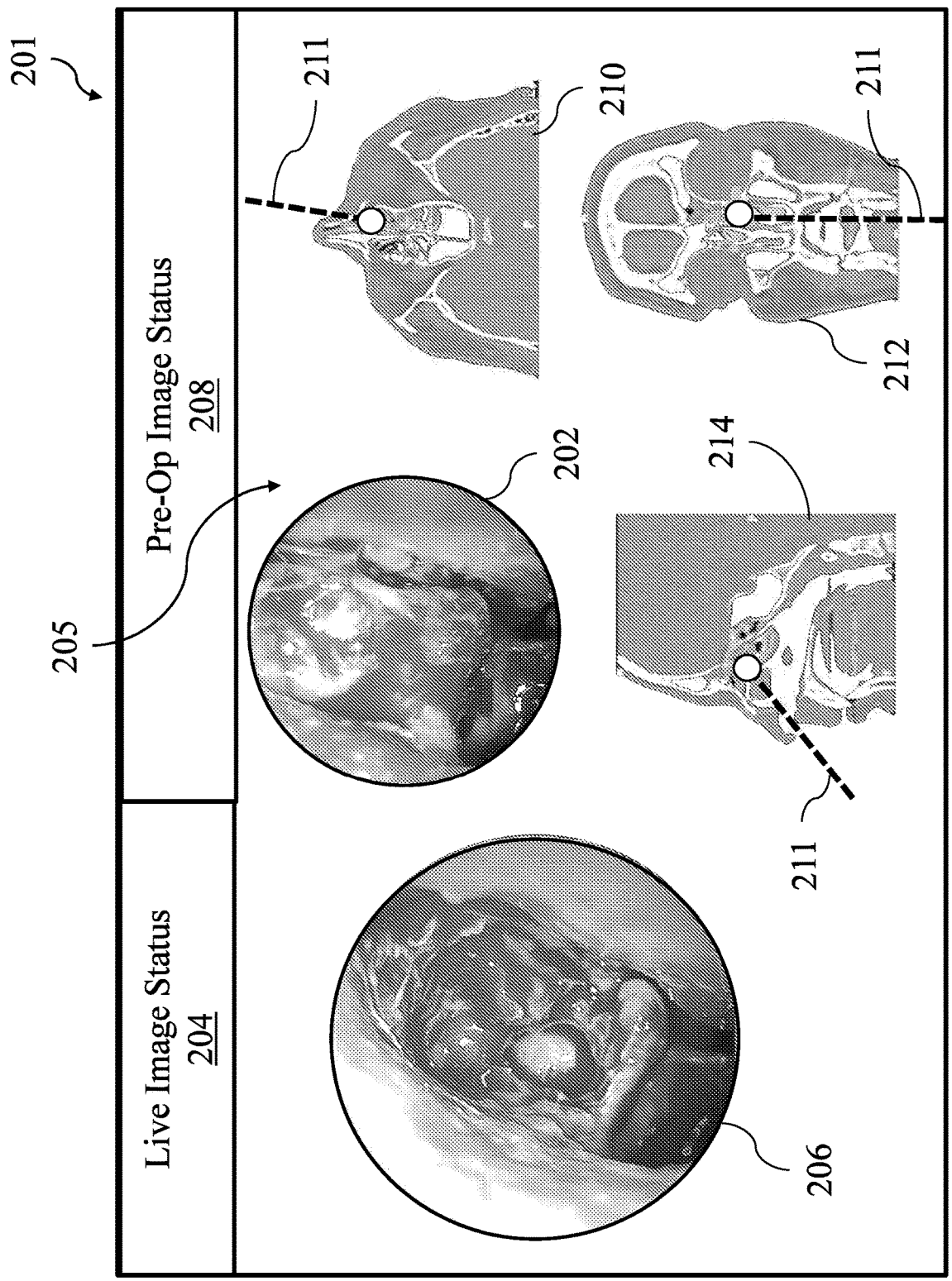
FIG. 4 depicts a simulated screenshot of an exemplary comparative interface with navigation images.
Figure 5:
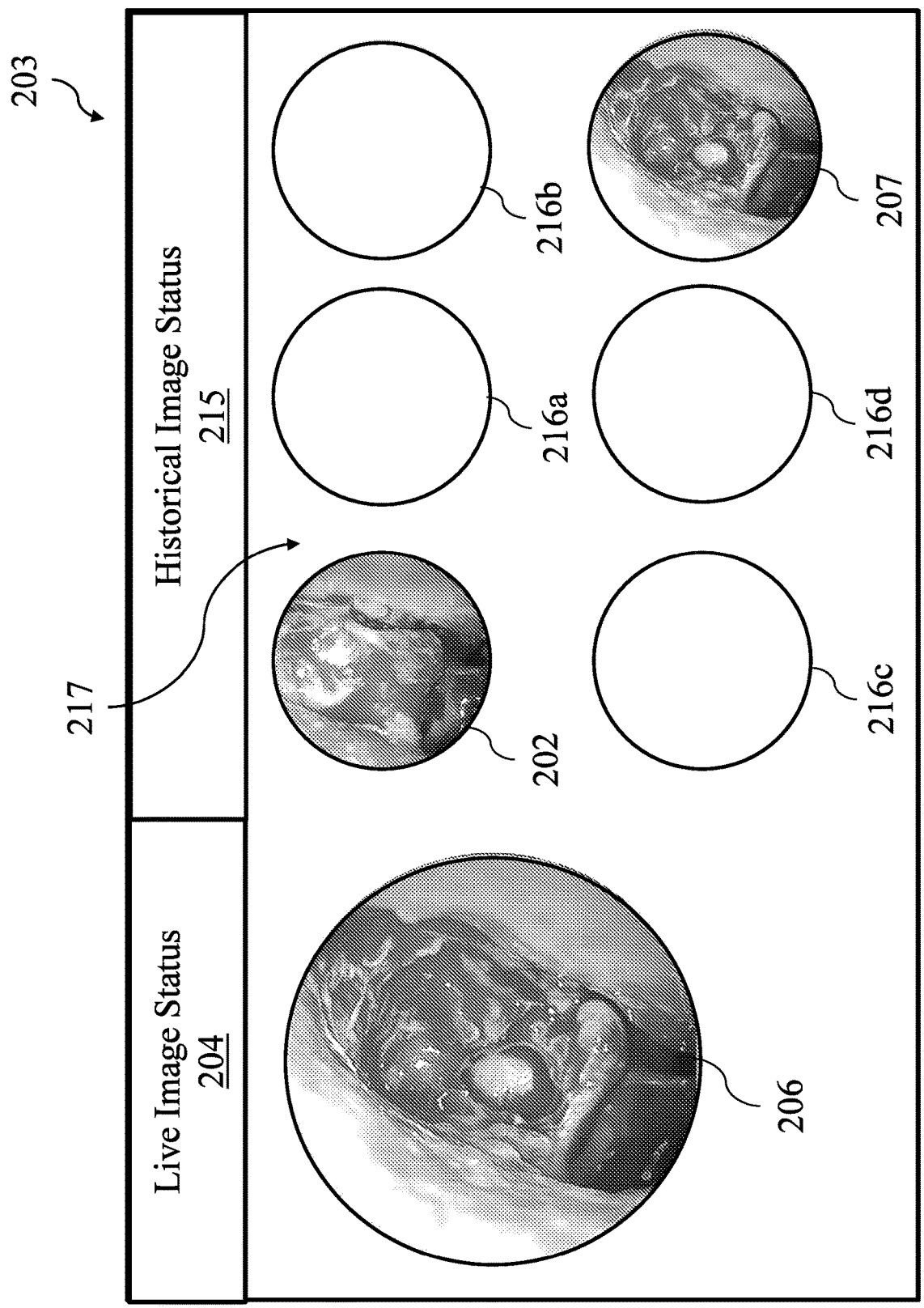
FIG. 5 depicts a simulated screenshot of an exemplary comparative interface with a chronological sequence of images.

For example, FIGS. 3-5 each show interfaces that may be displayed via a display such as the display screen (16) during IGS navigation in order to provide such additional context, while FIGS. 6-10 show sets of steps that may be performed to configure and provide one or more of the interfaces of FIGS. 3-5. In particular, FIG. 3 depicts a simulated screenshot of an exemplary comparative interface (200). The comparative interface (200) includes a pre-operative endoscopic image (202) and a pre-operative endoscopic image status (204), as well as a live endoscopic image (206) and a live endoscopic image status (208). It should be noted that, when used herein, describing an endoscopic image or information as being associated with a "pre-operative" timing of capture or status may indicate that the endoscopic image or status is captured before the start of a particular operation, such as during a consultation or exploratory imaging of a surgical site days or weeks prior to an operation; but may also indicate that the endoscopic image or status is captured at any time prior to a current or immediate stage of an operation, such as immediately prior to a first tissue modification made during a first stage of an operation, or immediately prior to a second tissue modification made during a second stage of an operation, or at other times. While FIG. 3 shows the live endoscopic image (206) and the pre-operative endoscopic image (202) displayed side by side, it should be understood that they may be displayed in various other ways in relation to each other, or may be overlapped (e.g., the pre-operative endoscopic image (202) may be modified to semi-transparency and overlaid upon the live endoscopic image (206)).

The pre-operative endoscopic image (202) may show a captured endoscopic image from a past moment in time (e.g., prior to the start of the current procedure, or during a prior stage of the current procedure), while the pre-operative endoscopic image status (204) may show one or more pieces of information associated with the pre-operative endoscopic image (202). For example, the pre-operative endoscopic image status (204) may include a three-dimensional position of the position sensor (104) at the time that the pre-operative endoscopic image (202) was captured, which may be displayed as information (e.g., x, y, and z-coordinates) or may be displayed as a simulated position relative to the surgical site (e.g., a rendered three-dimensional position of the position sensor (104) relative to the surgical site) at the time of capture.

The live endoscopic image (206) may show a captured endoscopic image from a present moment in time, such as one captured by the endoscope (100) during a present surgical procedure, while the live endoscopic image status (208) may show one or more pieces of information associated with the live endoscopic image (206). The live endoscopic image status (208) may show information similar to that shown in the pre-operative image status (204); and may include a three-dimensional position of the position sensor (104) at the time that the live endoscopic image (206) was captured as coordinates (e.g., x, y, and z-coordinates) or may be displayed as a simulated position relative to the surgical site.

While the live endoscopic image (206) shows a real-time image or video of the surgical site captured via the endoscope (100), the pre-operative endoscopic image (202) will show a past image or video of the surgical site captured from the same or similar perspective as that of the live endoscopic image (206) by comparing past and present position data from the position sensor (104) associated with each endoscopic image or video, as will be explained in greater detail below in FIGS. 6-10. With such an interface, as a surgeon moves the endoscope (100) (e.g. advances, withdraws, rotates in either direction, mechanically articulates in any direction) the real-time position data provided by the position sensor (104) will change as well as the real-time image shown in the live endoscopic image (206). As the real-time position data changes, the pre-operative endoscopic image (202) may also be updated based upon the real-time position data to show a previously captured image from the same or similar perspective as that indicated by the real-time position data.

As examples of the above, in some implementations, the pre-operative endoscopic image (202) may be updated automatically in response to changing position data, and may be presented as a sequence of images that appear to be a video of pre-operative endoscopic images, or as a still image when position data is not changing. In this manner, the pre-operative endoscopic image (202) may provide a similar perspective and view, captured pre-operatively, as that captured by the endoscope (100) in real-time. In some implementations, the pre-operative endoscopic image (202) may be presented as a still image that is manually updated by a user (e.g., based upon a button input, voice input, or other input) when desired, such that a user may position the endoscope (100) and then manually update the displayed pre-operative endoscopic image. In some implementations, the pre-operative endoscopic image (202) may be presented as a still image that is automatically updated based upon changing position data only when the endoscope (100) is not being substantially moved or positioned, such that the still image will automatically update after a purposeful movement of the endoscope (100) occurs and then ceases.

In some implementations, the pre-operative endoscopic image (202) may be presented as a looping sequence of images selected from the pre-operatively obtained images or video based upon the changing position data. This could include, for example, in response to a change in position data, displaying a sequence of images including a pre-operatively obtained endoscopic image associated with that position data, as well as several other pre-operatively obtained endoscopic images associated with nearby position data (e.g., from a slightly different position or orientation), which may provide a slight sense of movement around and with respect to the surgical site displayed by the pre-operative endoscopic image. Other techniques for displaying the pre-operative endoscopic image (202) exist and are described below, or will be apparent to those skilled in the art in view of the teachings herein.

In some implementations of such an interface, the pre-operative image status (204), live endoscopic image status (208), or both may provide information describing their perspective (e.g., a position and an orientation in three-dimensional space) relative to each other as numeric offsets or directional movement or rotations that may be performed to more accurately align the images. As an example, where the live endoscopic image (206) is captured from a perspective having position $x_1$, $y_1$, and $z_1$ and an orientation having $yaw_1$, $pitch_1$, and $roll_1$, there may not be a previously captured image from that exact perspective. Instead, a best match may be displayed having a perspective of $x_1$, $y_2$, and $z_1$, and an orientation of $yaw_1$, $roll_1$, and $pitch_2$. In such a case, the live endoscopic image status (208) may show numeric, textual, or directional information indicating changes that must be made to reduce or eliminate the difference between $y_1$ and $y_2$ (e.g., a directional arrow pointing upwards) and between $pitch_1$ and $pitch_2$ (e.g., a directional arrow indicating a rotational pitch upwards).

FIG. 4 shows a simulated screenshot of an exemplary alternate comparative interface (201) that may be displayed to a user of a system such as the IGS navigation system (10). The comparative interface (201) includes the live endoscopic image (206) and live endoscopic image status (204), and also includes the pre-operative image status (208) and a panel of pre-operative images (205) including the pre-operative endoscopic image (202). The panel of pre-operative images (205) also includes a set of digital scan images (e.g., CT or MRI, 3-D map, etc.) including a top down image (210), a front image (212), and a side image (214), each having an overlaid instrument position (211). The overlaid instrument position (211) may represent the real-time position of the endoscope (100) based upon the position sensor (104), and each of the digital scan images may be navigated with conventional means or controls (e.g., keyboard, mouse, touchscreen, or use of navigational arrows or controls); or may be automatically selected and displayed based upon data from the position sensor (104) (e.g., the top down image (210) may be selected based upon a determined x and z-coordinate, the front image (212) may be selected based upon a determined x and y-coordinate, and the side image (214) may be selected based upon a determined y and z-coordinate).

As with the example of FIG. 3, the pre-operative endoscopic image (202) may be selected and displayed based upon data from the position sensor (104) such that the perspective of the displayed endoscopic image matches or substantially matches the current perspective of the live endoscopic image (206) captured by the endoscope (100), based upon data from the position sensor (104). In this manner, as a surgeon moves the endoscope (100) and receives endoscopic images and video as the live endoscopic image (206), one or more images in the panel of pre-operative images (205) may also update to display a similar perspective, as will be described in more detail below.

FIG. 5 shows a simulated screenshot of an exemplary alternate comparative interface (203) that includes a chronological endoscopic image panel (217), in addition to the live endoscopic image (206) and the live endoscopic image status (204). The chronological image panel (217) may include a set of ordered endoscopic images (e.g., ordered by time of capture, stage of procedure) showing the surgical site at different moments occurring between an initial endoscopic image (e.g., the pre-operative endoscopic image (202), which may be captured prior to a procedure, or prior to a first tissue modification or step of a procedure) and a more recent endoscopic image (e.g., the live endoscopic image (206), or an endoscopic image (207) that may be the most recent endoscopic image captured or saved prior to the live endoscopic image (206)). A set of intervening endoscopic images (216a, 216b, 216c, 216d) may show one or more endoscopic images of the surgical site at varying times, from the similar or same perspective as shown in the pre-operative endoscopic image (202) and the live endoscopic image (206); and as shown may include a first endoscopic image (216a), a second endoscopic image (216b), a third endoscopic image (216c), and a fourth endoscopic image (216d). As with prior examples, the selection and display of endoscopic images in the chronological image panel (217) may be determined based upon data from the position sensor (100), such that those endoscopic images show the surgical site from a matching or substantially matching perspective as the live endoscopic image (206) currently captured by the endoscope (100).

For example, where a particular surgical procedure has five major steps, each intervening endoscopic image may show the surgical site after the completion of a step. In such an example, the pre-operative endoscopic image (202) might show the surgical site prior to any tissue modifications, the first endoscopic image (216a) might show the surgical site after a first set of tissue modifications during a first stage of the procedure, while the fourth endoscopic image (216d) might show the surgical site after a subsequent set of tissue modifications during a fourth stage of the procedure, and the endoscopic image (207) may show the surgical site after a set of tissue modifications at a final stage of the procedure.

As another example, one or more of the intervening endoscopic images may show the surgical site at various times as determined manually by a surgeon. In such an example, a surgeon may, by interacting with a button or control of the IGS navigation system (10) mark a current live endoscopic image (206) to be added to the set of intervening endoscopic images, which may allow the surgeon to choose certain milestone endoscopic images or other reference endoscopic images to be saved for future reference via the comparative interface (203). As yet another example, one or more intervening endoscopic images may show the surgical site at various times as determined automatically by the IGS navigation system (10) or another tool or device in use during the procedure. In such an example, endoscopic images may be automatically added to the intervening endoscopic images based upon information or activity from a surgical instrument, surgical instrument generator, or another device. This could include capturing an endoscopic image whenever a cutting tool is activated, so that a set of intervening endoscopic images is automatically built showing the surgical site prior to each tissue modification or activation. As yet another example, endoscopic images may be captured and added to the intervening endoscopic images based upon a passage of time (e.g., endoscopic images may be regularly captured and added to the intervening endoscopic images based on a configurable schedule).

In any case, the set of intervening endoscopic images may be sized and arranged for display in varying ways, including as one or more of the below examples. In some implementations, the endoscopic images may be sized and arranged so that each is displayed simultaneously via the comparative interface (203). In some implementations, the endoscopic images may be horizontally or laterally scrolled or traversed through based upon a user input, which may accommodate for a large set of intervening endoscopic images. In some implementations, the endoscopic images may be displayed using various digital manipulations. This may include, for example, display as a video sequence (e.g., each endoscopic image may be briefly displayed in sequence to create a visual sense of watching a video rather than viewing a number of isolated images), or displayed using image morphing (e.g., where a first endoscopic image and a second endoscopic image are used to produce and display a number of intervening endoscopic images which create a visual sense of the pre-operatively obtained endoscopic image gradually morphing into the current or otherwise more recent endoscopic image).

The comparative interface (203) also includes a chronology status (215) which may show information similar to the pre-operative endoscopic image status (208), and may additionally show chronology related information such as the time when each of the intervening endoscopic image was captured (e.g., a time in hours and minutes, a duration of time since capture, a stage of the procedure in which the image was captured) and the circumstances of its capture (e.g., whether it was added manually or automatically, and under what conditions or in response to what occurrences).

III. EXEMPLARY METHODS FOR COMPARATIVE NAVIGATION

Figure 6:
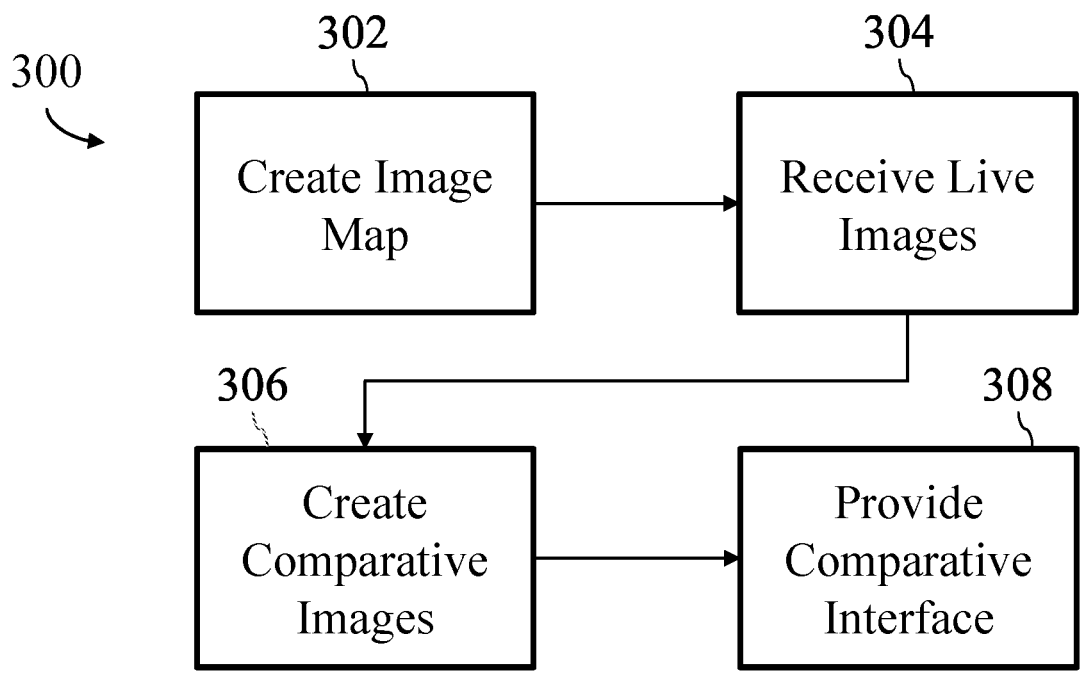
FIG. 6 shows a flowchart of an exemplary set of high level steps that may be performed to provide the comparative interface of any of FIGS. 3-5.

While FIGS. 3-5 show variations on comparative interfaces that may be provided by a system such as the IGS navigation system (10), FIGS. 6-10 show steps that may be performed by such a system to configure and display those interfaces. For example, FIG. 6 shows a flowchart of an exemplary set of high level steps (300) that may be performed to provide the comparative interface of any of FIGS. 3-5. These steps include creating (block 302) an endoscopic image map of pre-operative endoscopic images (e.g., past endoscopic images, previously captured endoscopic images, or historical endoscopic images), which may include using the endoscope (100) prior to the start of a procedure to capture endoscopic images of the surgical site from a number of different perspectives (e.g., different locations and orientations relative to the surgical site), in order to create a set of endoscopic images and associated position or perspective data. The system may also receive (block 304) live endoscopic images during a procedure via the endoscope (100), with such live endoscopic images also being associated with position or perspective data. The system may then create (block 306) one or more comparative endoscopic images based upon the endoscopic image map and the live endoscopic images, which may include selecting a matching endoscopic image from the endoscopic image map and using it without modification; or modifying or combining one or more endoscopic images from the endoscopic image map to provide as a comparative image. With one or more created (block 306) comparative endoscopic images, the system may then provide (block 308) a comparative interface via a display such as the display screen (16) including any combination of the features shown and described herein.

Figure 7:
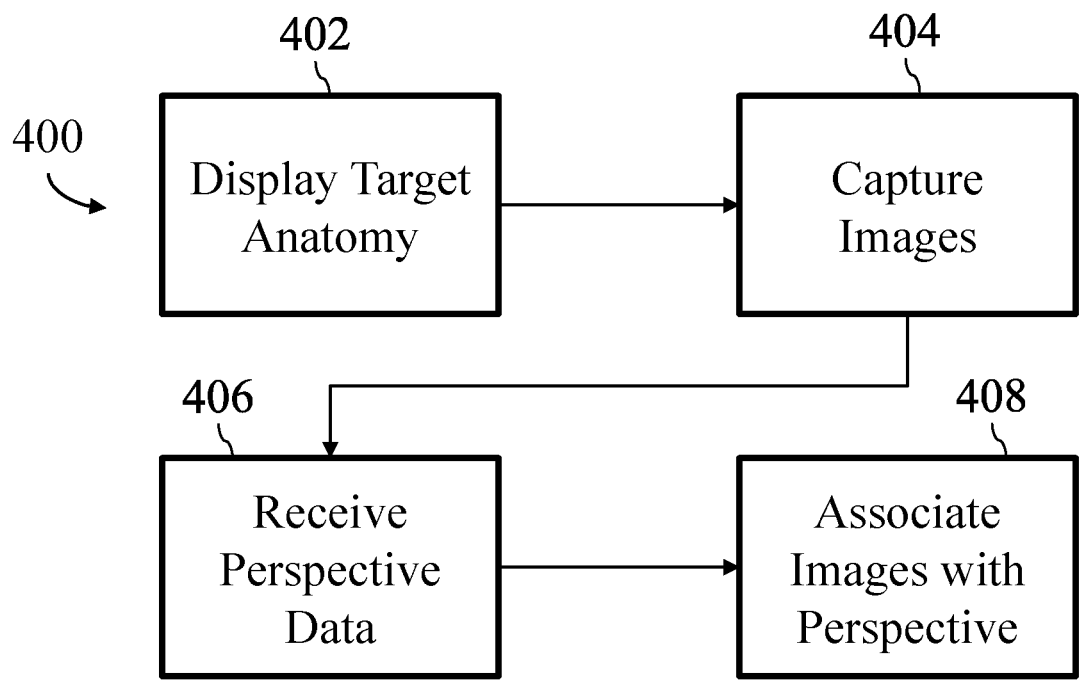
FIG. 7 shows a flowchart of an exemplary set of steps that may be performed to create an image navigation map.

FIG. 7 shows a flowchart of an exemplary set of steps (400) that may be performed during a step such as creating (block 302) the endoscopic image map. The endoscope (100) may be navigated to the surgical site and the system may display (block 402) the target anatomy at the surgical site as the endoscope (100) captures (block 404) a set of endoscopic images of the target anatomy. As each endoscopic image is captured by the endoscope (100), the system may receive (block 406) perspective data (e.g., position, orientation, or both) from the position sensor (104) and associate (block 408) the perspective data with the corresponding endoscopic image. The result is a set of endoscopic images of the target anatomy, with each endoscopic image being associated with a perspective, relative to the target anatomy, at the moment of capture. Endoscopic images may be captured by the endoscope as still endoscopic images; or as a video sequence of endoscopic images/frames, as may be desirable to achieve a particular resolution, clarity, or focus of the resulting endoscopic image sets.

In some implementations, the system may identify and discard duplicate (e.g., two endoscopic images captured from the exact same perspective) or substantially duplicate endoscopic images (e.g., two endoscopic images being captured from two different perspectives that are not visually distinct from each other) from the resulting endoscopic image set in order to reduce the overall size and contents of the endoscopic image map.

In some implementations, the system may determine that an endoscopic image from a first perspective can be modified to provide a substantially duplicate endoscopic image from a second perspective. For example, where the second perspective is linearly or substantially linearly positioned between the first perspective and the target anatomy, an endoscopic image from the second perspective may appear to be a zoomed, magnified, or more proximate endoscopic image of the target anatomy from the first perspective. In other words, an endoscopic image of the target anatomy captured from the most distal perspective can be cropped and enlarged (e.g., either modified before being added to the endoscopic image map, or being modified in real-time as they are selected from the endoscopic image map) to simulate an endoscopic image from each perspective in between the most distal perspective and the target anatomy, which may further reduce the size and contents of the endoscopic image map, and may also reduce the need to navigate the endoscope (100) to each and every distinct perspective during creation of the endoscopic image map (e.g., if endoscopic images are captured from multiple distal perspectives, more proximal perspectives can be simulated rather than requiring the endoscope (100) be advanced toward the target anatomy).

During capture (block 404) of the pre-operative endoscopic images, the system may provide instructions to a user of the endoscope (100) indicating perspectives that have already been captured, and perspectives that have not yet been captured. This may include, for example, directional prompts indicating that the endoscope (100) should be moved or rotated to capture endoscopic images from a desired perspective (e.g., where the system has been configured by a user or based upon a certain procedure to capture endoscopic images from ten different perspectives around the surgical site). As another example, this may include displaying a three-dimensional sphere or other object with a representation of the target anatomy located within at a fixed point; and rendering regions of the object for which a perspective has been captured as being visually distinct from regions where a perspective has not been captured. With such a system, a user of the endoscope (100) may reference the rendered three-dimensional object to aid in navigating the endoscope (100) to different perspectives in order to capture an endoscopic image from that perspective.

Once captured and associated with perspective data, the set of endoscopic images may be stored in varying ways, such as a database where endoscopic images may be selected based upon an exact or partial match of perspective data used in a query; or may be compiled into an object or software module that may receive perspective data as input and provide a matching or similar endoscopic image in response.

Figure 8:
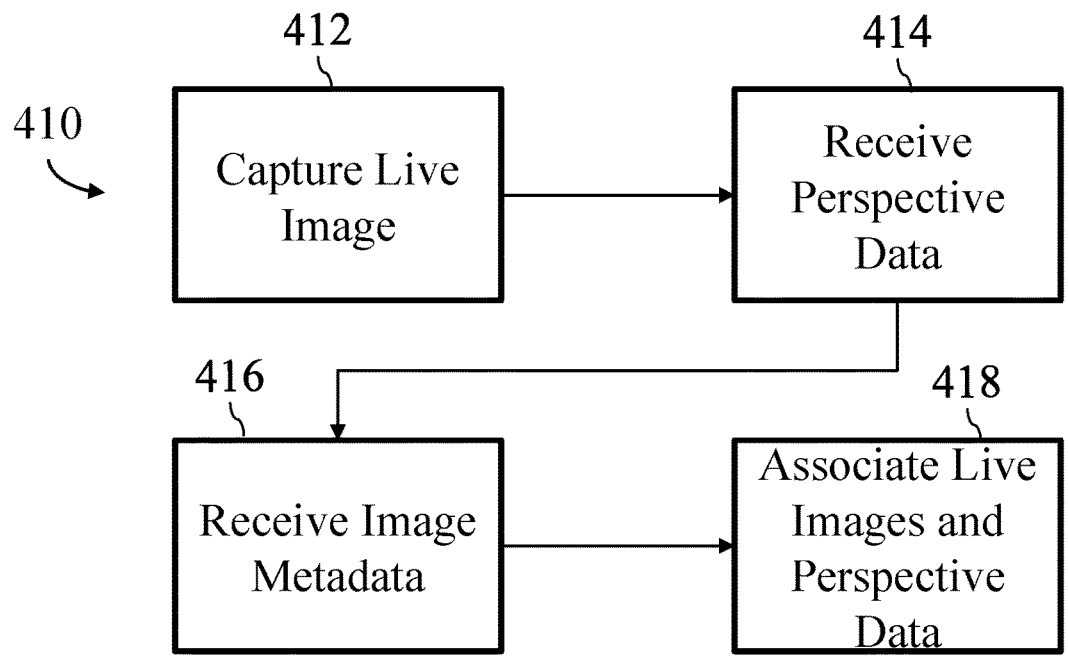
FIG. 8 shows a flowchart of an exemplary set of steps that may be performed to capture live images during a procedure.

FIG. 8 shows a flowchart of an exemplary set of steps (410) that may be performed during a step such as receiving (block 304) live endoscopic images during a medical procedure. When the endoscope (100) is positioned during a medical procedure, it may capture (block 412) live endoscopic images of the surgical site in real-time in order to display such information via the display screen (16). The IGS navigation system (10) may be configured to track the position of the endoscope (100) via the position sensor (104) during the procedure in order to provide normal IGS navigation tracking of the instrument (e.g., in order to provide features such as the overlaid instrument position (211)). Such data, which may conventionally be used solely for tracking, may also be received (block 414) as perspective data and retained or stored in order to provide one or more features of a comparative interface.

The system may also receive (block 416) one or more pieces of metadata associated with a captured (block 412) endoscopic image, which may include, for example, a time of capture, a stage of a procedure during capture, an instrument status during capture (e.g., whether a cutting device is activated during capture), or a manual input from a surgeon tagging or otherwise associated a captured (block 412) endoscopic image with a certain characteristic (e.g., marking a captured endoscopic image to be displayed as an intervening endoscopic image in the chronological image panel (217)). When received (block 416) endoscopic image metadata indicates that a particular live endoscopic image is being tagged or saved (e.g., as a result of user input or automatically based upon activation of an instrument, completion of a stage of a procedure, or other circumstances as have been described), that endoscopic image may be added to the endoscopic image map for future matching and display (e.g., via the comparative interface (203)). The system may then associate (block 418) the captured (block 412) live endoscopic image with perspective data, metadata, or both, which may include storing or converting the endoscopic image and data in a form that can be efficiently compared to, queried against, or otherwise evaluated against a created (block 302) image map in order to identify a prior endoscopic image that matches or substantially matches that captured (block 412) live endoscopic image.

Figure 9:
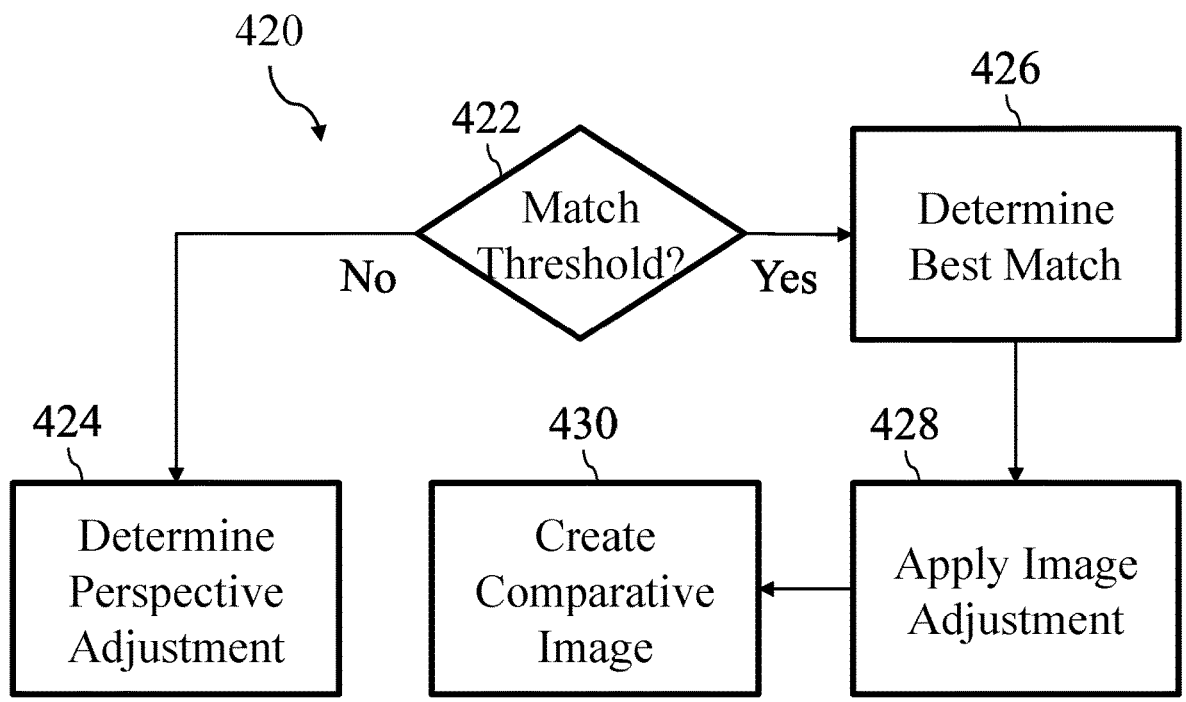
FIG. 9 shows a flowchart of an exemplary set of steps that may be performed to create comparative images.

FIG. 9 shows a flowchart of an exemplary set of steps (420) that may be performed during a step such as creating (block 306) comparative endoscopic images. Once associated (block 418) with perspective data, a live endoscopic image may be compared to the created (block 302) endoscopic image map to determine if the endoscopic image map contains one or more endoscopic images whose perspectives match or substantially match the perspective from which the immediate live endoscopic image was captured. A perspective that matches or substantially matches the perspective of a live endoscopic image may be determined to be above a configured match threshold (block 422). The match threshold may be manually configured to allow for a variance in perspective when determining if a good endoscopic image match exists for a live endoscopic image within the endoscopic image map. The allowable variance in perspective may be expressed per coordinate (e.g., a variance in x, y, or z-coordinate may be considered an acceptable match if the difference is 5 mm or less, or a variance in yaw, pitch, or roll may be considered an acceptable match if the difference is 10 degrees or less) or as an aggregate of difference across all coordinates (e.g., a minor difference in x-coordinate may be acceptable, while minor differences in x, y, and z-coordinates may be unacceptable).

Where no endoscopic image within the image map meets the match threshold, the system may determine (block 422) that there is no good match; and determine (block 424) an adjustment in perspective that may be made in order to place the endoscope (100) at a perspective where the endoscopic image map does contain good endoscopic image matches. This may include, for example, identifying one or more endoscopic images within the endoscopic image map that fall below the match threshold (block 422), but which are the next best matches, and then providing instructions via the display screen (16) for navigating the endoscope (100) to one or more of those perspectives (e.g., by providing numeric information or directional arrows showing a change in position, orientation, or both).

Where one or more endoscopic images that are above the match threshold (block 422) are determined to be within the endoscopic image map, the system may determine (block 426) the best or closest match (e.g., where several images are above the threshold, the image whose perspective has the least difference per-coordinate or aggregate difference across all coordinates). In some cases, the system may perform (block 428) one or more endoscopic image manipulation or image interpolation processes in order to prepare the determined (block 426) best match for display. This may include modifying the pre-operatively obtained endoscopic image in one or more ways to provide a better comparative image for the live endoscopic image, and may include, for example, adjusting the size or resolution of the pre-operatively obtained endoscopic image, smoothing or blurring the pre-operatively obtained endoscopic image, cropping the pre-operatively obtained endoscopic image, adjusting color, brightness, or tone of the pre-operatively obtained endoscopic image, and other changes in order to better visually match the live endoscopic image captured via the endoscope (100). This may also include combining (e.g., using image morphing, blending, or other techniques for combining two images from slightly different perspectives) one or endoscopic images that are equal or near-equal in being determined (block 426) as best matches. After performing (block 428) any needed adjustments, the system may then create (block 430) a comparative output endoscopic image suitable for display via a comparative interface, which may include, for example, converting the final adjusted endoscopic image to a particular format suitable for display.

Figure 10:
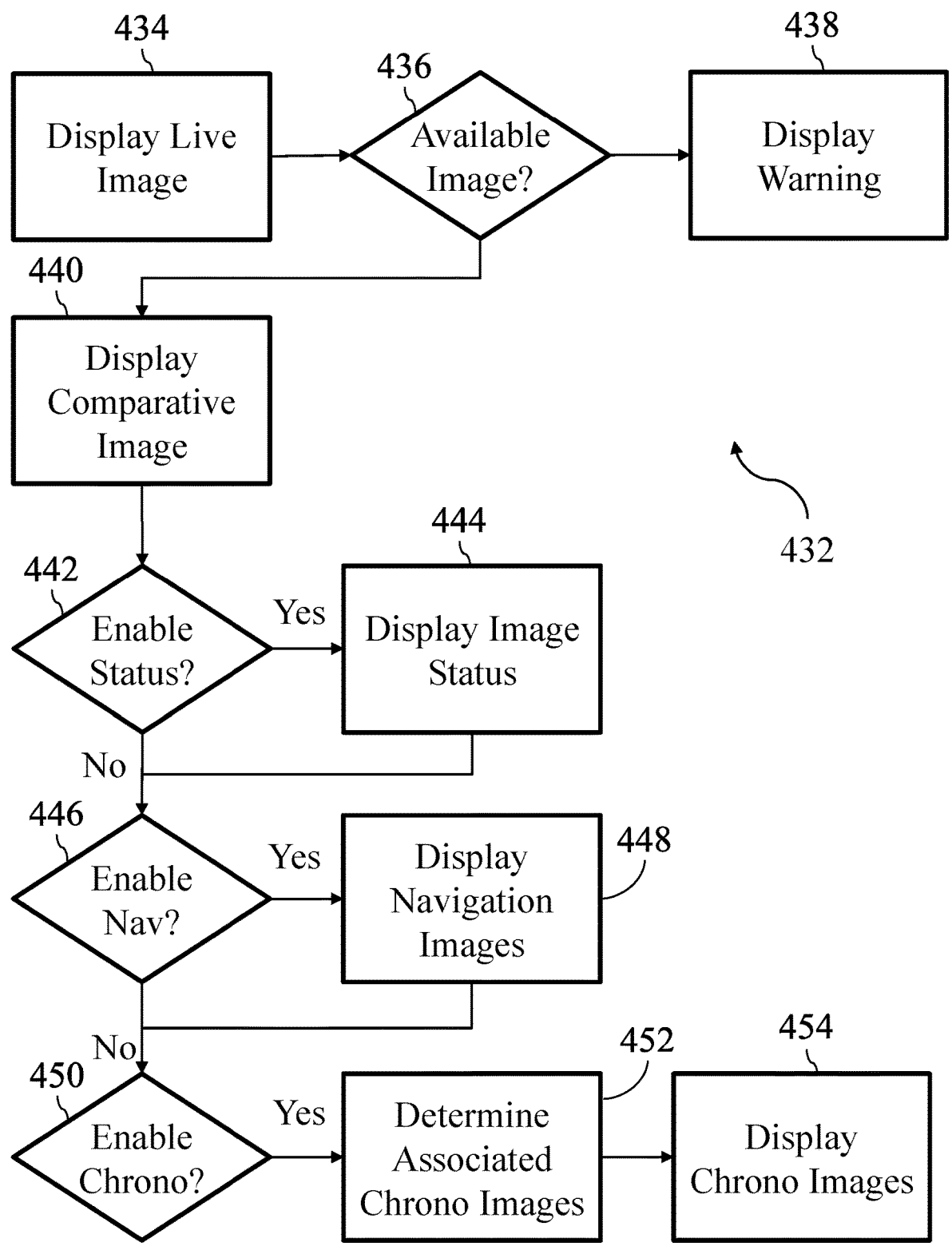
FIG. 10 shows a flowchart of an exemplary set of steps that may be performed to display information via the comparative interface of any of FIGS. 3-5.

FIG. 10 shows a flowchart of an exemplary set of steps (432) that may be performed to display information via a comparative interface having one or more features such as those shown in FIGS. 3-5. When providing a comparative interface, the system may display (block 434) a live endoscopic image, such as may be captured via the endoscope (100) and displayed as the live endoscopic image (206). Where a comparative, pre-operatively obtained endoscopic image is available (block 436) or can be created, as described in FIGS. 6-9 (e.g., by identifying (block 426) a best match and preparing it for display), the system may also display (block 440) the comparative endoscopic image, which may be displayed as the pre-operative endoscopic image (202). Where a suitable matching endoscopic image is not available (block 436), the system may display (block 438) a warning indicating that the endoscopic image map does not contain pre-operatively obtained endoscopic images from perspective suitable for display, may provide information (e.g., directional arrows) to aid a user in navigating the endoscope (100) to a perspective for which suitable endoscopic images are available, or both.

When displaying (block 434) the live endoscopic image and displaying (block 440) the comparative pre-operatively obtained endoscopic image, the system may provide additional features and information such as those shown in the comparative interfaces of FIGS. 3-5. Such features may be statically enabled or configured for particular interface; or may be enabled or disabled by a user during operation. For example, status information may be enabled (block 442) in order to display (block 444) status information for the live endoscopic image, comparative endoscopic image or both, which may include one or more of the pre-operative endoscopic image status (204), the live endoscopic image status (208), and the chronology status (215). As another example, navigational images may be enabled (block 446) in order to display (block 440) the comparative endoscopic image, display (block 434) the live endoscopic image, and display (block 448) a set of associated navigation images, such as the panel of pre-operative endoscopic images (205).

As another example, chronological image display may be enabled (block 450).

When enabled, the system may determine (block 452) a set of chronological endoscopic images associated with the perspective of the current live image (e.g., by performing steps such as those shown in FIG. 9 to match and prepare a plurality of endoscopic images from different moments in time), and then display (block 454) those endoscopic images as a video sequence, a morphing endoscopic image, or as intervening endoscopic images in the chronological image panel (217), as has been described.

IV. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An image guided surgery (IGS) navigation system comprising: an endoscope comprising a camera and a tracking sensor, wherein the tracking sensor is configured to interact with a tracked area; a processor configured to track the camera based upon an interaction of the tracking sensor with the tracked area; and a display; wherein the processor is further configured to: receive a past image of a surgical site of a patient, wherein the past image is captured by the camera at a first time, determine a set of past image tracking data for the camera at the first time, add the past image and the set of past image tracking data to an image map as a past perspective, wherein the image map comprises a plurality of past perspectives of the surgical site, and each past perspective of the plurality of past perspectives comprises: an image of the surgical site captured from a perspective, and a set of tracking data associated with the perspective, receive an operative image of the surgical site, wherein the operative image is captured by the camera at a second time, determine a set of live image tracking data for the camera at the second time, determine a matching perspective of the plurality of past perspectives based on the set of live image tracking data and the set of tracking data of the matching perspective, and display the operative image and the image of the surgical site of the matching perspective via the display.

Example 2

The IGS navigation system of Example 1, wherein the processor comprises a computer positioned within a surgical suite where the IGS navigation system is usable and a remote computer positioned outside of the surgical suite; wherein the tracked area comprises a magnetic field provided by a tracking field generator; and wherein the set of past image tracking data describes a position and an orientation of the camera.

Example 3

The IGS navigation system of any one or more of Examples 1 through 2, wherein the processor is further configured to: receive a subsequent operative image of the surgical site, determine a subsequent set of live image tracking data for the subsequent operative image, redetermine the matching perspective based on the subsequent set of live image tracking data, and in response to receiving one or more subsequent operative images, display each subsequent operative image and the image of the surgical site of the matching perspective via the display in near real-time.

Example 4

The IGS navigation system of any one or more of Examples 1 through 3, wherein the processor is further configured to, when determining the matching perspective: query the image map based on each position and orientation coordinate of the set of live image tracking data to determine a best match perspective, determine an offset for each position and orientation coordinate of the best match perspective relative to the set of live image tracking at, and select the best match perspective as the matching perspective when the offset is within a configured acceptable match threshold.

Example 5

The IGS navigation system of any one or more of Examples 1 through 4, wherein the processor is further configured to display an image status, wherein the image status comprises a comparison of the set of live image tracking data and the set of tracking data of the matching perspectives that indicates an offset of a live perspective of the operative image relative to the perspective of the matching perspective.

Example 6

The IGS navigation system of any one or more of Examples 1 through 5, wherein the processor is further configured to simultaneously display the operative image and the image of the surgical site of the matching perspective.

Example 7

The IGS navigation system of Example 6, wherein the processor is further configured to display the image of the surgical site of the matching perspective within a panel of pre-operative images, wherein the panel of pre-operative images further comprises at least three digital scan images of the patient, and wherein each of the at least three digital scan images comprises an overlaid instrument position.

Example 8

The IGS navigation system of any one or more of Examples 1 through 7, wherein the processor is further configured to: determine that the operative image should be retained as an intervening image, add the operative image, the set of live image tracking data, and the second time to the image map as an intervening perspective, determine one or more matching intervening perspectives of the image map based on the set of live image tracking data and a set of intervening tracking data associated with each intervening perspective, and display a set of intervening images of the one or more matching intervening perspectives.

Example 9

The IGS navigation system of Example 8, wherein the processor is further configured to determine that the operative image should be retained as an intervening image based upon an activation status of a surgical cutting instrument.

Example 10

The IGS navigation system of any one or more of Examples 8 through 9, wherein each intervening image of the set of intervening images is individually displayed as a video sequence ordered by a time of capture associated with each intervening image.

Example 11

The IGS navigation system of any one or more of Examples 8 through 10, wherein each intervening image of the set of intervening images is individually displayed as a gradual image morph ordered by a time of capture associated with each intervening image.

Example 12

The IGS navigation system of any one or more of Examples 1 through 11, wherein the processor is further configured to, where the matching perspective cannot be determined, display a message via the display indicating a change in perspective of the camera that would result in the matching perspective being available in the image map.

Example 13

The IGS navigation system of any one or more of Examples 1 through 12, wherein the processor is further configured to: receive a second past image of the surgical site and determine a perspective associated with the second past image based upon a second set of past image tracking data, determine whether the perspective associated with the second past image is a duplicate of a perspective already within the plurality of past perspectives of the surgical site, and only add the second past image to the plurality of past perspectives where the perspective is not a duplicate.

Example 14

A method for providing a comparative interface during image guided (IGS) navigation surgery comprising: at a processor: receiving a past image of a surgical site of a patient, wherein the past image is captured by a camera of an endoscope at a first time, and determining a set of past image tracking data for the camera at the first time based upon a tracking sensor of the endoscope; adding the past image and the set of past image tracking data to an image map as a past perspective, wherein the image map comprises a plurality of past perspectives of the surgical site, and each past perspective of the plurality of past perspectives comprises: an image of the surgical site captured from a perspective, and a set of tracking data associated with the perspective, receiving an operative image of the surgical site, wherein the operative image is captured by the camera at a second time, and determining a set of live image tracking data for the camera at the second time; determining a matching perspective of the plurality of past perspectives based on the set of live image tracking data and the set of tracking data of the matching perspective; and displaying the operative image and the image of the surgical site of the matching perspective via a display.

Example 15

The method of Example 14, further comprising: receiving a subsequent operative image of the surgical site and determining a subsequent set of live image tracking data for the subsequent operative image; redetermining the matching perspective based on the subsequent set of live image tracking data; and in response to receiving one or more subsequent operative images, displaying each subsequent operative image and the image of the surgical site of the matching perspective via the display in real-time.

Example 16

The method of any one or more of Examples 14 through 15, further comprising, when determining the matching perspective: querying the image map based on each position and orientation coordinate of the set of live image tracking data to determine a best match perspective, determining an offset for each position and orientation coordinate of the best match perspective relative to the set of live image tracking at, and selecting the best match perspective as the matching perspective when the offset is within a configured acceptable match threshold.

Example 17

The method of any one or more of Examples 14 through 16, further comprising simultaneously displaying the operative image and the image of the surgical site of the matching perspective.

Example 18

The method of Example 17, further comprising displaying the image of the surgical site of the matching perspective within a panel of pre-operative images, wherein the panel of pre-operative images further comprises at least three digital scan images of the patient, and wherein each of the at least three digital scan images comprises an overlaid instrument position.

Example 19

The method of any one or more of Examples 14 through 18, further comprising, where the matching perspective cannot be determined, displaying a message via the display indicating a change in perspective of the camera that would result in the matching perspective being available in the image map.

Example 20

A processor configured to: receive a past image of a surgical site of a patient, wherein the past image is captured by a camera at a first time; determine a set of past image tracking data for the camera at the first time; add the past image and the set of past image tracking data to an image map as a past perspective, wherein the image map comprises a plurality of past perspectives of the surgical site, and each past perspective of the plurality of past perspectives comprises: an image of the surgical site captured from a perspective, and a set of tracking data associated with the perspective; receive an operative image of the surgical site, wherein the operative image is captured by the camera at a second time; determine a set of live image tracking data for the camera at the second time; determine a matching perspective of the plurality of past perspectives based on the set of live image tracking data and the set of tracking data of the matching perspective; and display the operative image and the image of the surgical site of the matching perspective via the display.

V. MISCELLANEOUS

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one skilled in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An image guided surgery (IGS) navigation system comprising:
    (a) an endoscope comprising a camera and a tracking sensor, wherein the tracking sensor is configured to interact with a tracked area;
    (b) a processor configured to track the camera based upon an interaction of the tracking sensor with the tracked area; and
    (c) a display;
    wherein the processor is further configured to:
        (i) receive a past image of a surgical site of a patient, wherein the past image is captured by the camera at a first time,
        (ii) determine a set of past image tracking data for the camera at the first time,
        (iii) add the past image and the set of past image tracking data to an image map as a past perspective, wherein the image map comprises a plurality of past perspectives of the surgical site, and each past perspective of the plurality of past perspectives comprises:
            (A) an image of the surgical site captured from a perspective, and
            (B) a set of tracking data associated with the perspective,
        (iv) receive an operative image of the surgical site, wherein the operative image is captured by the camera at a second time,
        (v) determine a set of live image tracking data for the camera at the second time,
        (vi) determine a matching perspective of the plurality of past perspectives based on a comparison between a threshold distance and an offset, the offset being a distance between the set of live image tracking data and the set of tracking data of the matching perspective, and (vii) display the operative image and the image of the surgical site of the matching perspective via the display.

2. The IGS navigation system of claim 1, wherein the processor comprises a computer positioned within a surgical suite where the IGS navigation system is usable and a remote computer positioned outside of the surgical suite;
wherein the tracked area comprises a magnetic field provided by a tracking field generator; and
wherein the set of past image tracking data describes a position and an orientation of the camera.

3. The IGS navigation system of claim 1, wherein the processor is further configured to:
(i) receive a subsequent operative image of the surgical site,
(ii) determine a subsequent set of live image tracking data for the subsequent operative image,
(iii) redetermine the matching perspective based on the subsequent set of live image tracking data, and
(iv) in response to receiving one or more subsequent operative images, display each subsequent operative image and the image of the surgical site of the matching perspective via the display in near real-time.

4. The IGS navigation system of claim 1, wherein the processor is further configured to, when determining the matching perspective:
(i) query the image map based on position and orientation coordinates of the set of live image tracking data to determine a best match perspective,
(ii) determine an offset for each position and orientation coordinate of the best match perspective relative to the set of live image tracking at, and
(iii) select the best match perspective as the matching perspective when the offset is within the threshold distance.

5. The IGS navigation system of claim 1, wherein the processor is further configured to display an image status, wherein the image status comprises a comparison of the set of live image tracking data and the set of tracking data of the matching perspectives that indicates the offset of a live perspective of the operative image relative to the perspective of the matching perspective.

6. The IGS navigation system of claim 1, wherein the processor is further configured to simultaneously display the operative image and the image of the surgical site of the matching perspective.

7. The IGS navigation system of claim 6, wherein the processor is further configured to display the image of the surgical site of the matching perspective within a panel of pre-operative images, wherein the panel of pre-operative images further comprises at least three digital scan images of the patient, and wherein each of the at least three digital scan images comprises an overlaid instrument position.

8. The IGS navigation system of claim 1, wherein the processor is further configured to:
(i) determine that the operative image should be retained as an intervening image,
(ii) add the operative image, the set of live image tracking data, and the second time to the image map as an intervening perspective,
(iii) determine one or more matching intervening perspectives of the image map based on the set of live image tracking data and a set of intervening tracking data associated with each intervening perspective, and
(iv) display a set of intervening images of the one or more matching intervening perspectives.

9. The IGS navigation system of claim 8, wherein the processor is further configured to determine that the operative image should be retained as an intervening image based upon an activation status of a surgical cutting instrument.

10. The IGS navigation system of claim 8, wherein each intervening image of the set of intervening images is individually displayed as a video sequence ordered by a time of capture associated with each intervening image.

11. The IGS navigation system of claim 8, wherein each intervening image of the set of intervening images is individually displayed as a gradual image morph ordered by a time of capture associated with each intervening image.

12. The IGS navigation system of claim 1, wherein the processor is further configured to, where the matching perspective cannot be determined, display a message via the display indicating a change in perspective of the camera that would result in the matching perspective being available in the image map.

13. The IGS navigation system of claim 1, wherein the processor is further configured to:
(i) receive a second past image of the surgical site and determine a perspective associated with the second past image based upon a second set of past image tracking data,
(ii) determine whether the perspective associated with the second past image is a duplicate of a perspective already within the plurality of past perspectives of the surgical site, and
(iii) only add the second past image to the plurality of past perspectives where the perspective is not a duplicate.

14. A method for providing a comparative interface during image guided (IGS) navigation surgery comprising:
(a) at a processor:
(i) receiving a past image of a surgical site of a patient, wherein the past image is captured by a camera of an endoscope at a first time, and
(ii) determining a set of past image tracking data for the camera at the first time based upon a tracking sensor of the endoscope;
(b) adding the past image and the set of past image tracking data to an image map as a past perspective, wherein the image map comprises a plurality of past perspectives of the surgical site, and each past perspective of the plurality of past perspectives comprises:
(i) an image of the surgical site captured from a perspective, and
(ii) a set of tracking data associated with the perspective,
(c) receiving an operative image of the surgical site, wherein the operative image is captured by the camera at a second time, and determining a set of live image tracking data for the camera at the second time;
(d) determining a matching perspective of the plurality of past perspectives based on a comparison between a threshold distance and an offset, the offset being a distance between the set of live image tracking data and the set of tracking data of the matching perspective; and
(e) displaying the operative image and the image of the surgical site of the matching perspective via a display.

15. The method of claim 14, further comprising:
(a) receiving a subsequent operative image of the surgical site and determining a subsequent set of live image tracking data for the subsequent operative image;

(b) redetermining the matching perspective based on the subsequent set of live image tracking data; and (c) in response to receiving one or more subsequent operative images, displaying each subsequent operative image and the image of the surgical site of the matching perspective via the display in real-time.

16. The method of claim 14, further comprising, when determining the matching perspective:

(i) querying the image map based on position and orientation coordinates of the set of live image tracking data to determine a best match perspective, (ii) determining an offset for each position and orientation coordinate of the best match perspective relative to the set of live image tracking at, and (iii) selecting the best match perspective as the matching perspective when the offset is within the threshold distance.

17. The method of claim 14, further comprising simultaneously displaying the operative image and the image of the surgical site of the matching perspective.

18. The method of claim 17, further comprising displaying the image of the surgical site of the matching perspective within a panel of pre-operative images, wherein the panel of pre-operative images further comprises at least three digital scan images of the patient, and wherein each of the at least three digital scan images comprises an overlaid instrument position.

19. The method of claim 14, further comprising, where the matching perspective cannot be determined, displaying a message via the display indicating a change in perspective of the camera that would result in the matching perspective being available in the image map.

20. A processor configured to:

(a) receive a past image of a surgical site of a patient, wherein the past image is captured by a camera at a first time;

(b) determine a set of past image tracking data for the camera at the first time;

(c) add the past image and the set of past image tracking data to an image map as a past perspective, wherein the image map comprises a plurality of past perspectives of the surgical site, and each past perspective of the plurality of past perspectives comprises:

(i) an image of the surgical site captured from a perspective, and (ii) a set of tracking data associated with the perspective;

(d) receive an operative image of the surgical site, wherein the operative image is captured by the camera at a second time;

(e) determine a set of live image tracking data for the camera at the second time;

(f) determine a matching perspective of the plurality of past perspectives based on the set of live image tracking data and the set of tracking data of the matching perspective;

(g) manipulate the past image of the surgical site of the matching perspective to provide a manipulated past image which is closer in comparison to the operative image than the past image; and (h) display the operative image and the manipulated past image of the surgical site of the matching perspective via the display.

* * * * *